US008546581B2

(12) United States Patent
Jungheim et al.

(10) Patent No.: US 8,546,581 B2
(45) Date of Patent: Oct. 1, 2013

(54) COMPOUNDS, METHODS AND FORMULATIONS FOR THE ORAL DELIVERY OF A GLUCAGON-LIKE PEPTIDE (GLP)-1 COMPOUND OR A MELANOCORTIN-4 RECEPTOR (MC4) AGONIST PEPTIDE

(75) Inventors: Louis Nickolaus Jungheim, Indianapolis, IN (US); John Mcneill McGill, III, Greenwood, IN (US); Kenneth Jeff Thrasher, Indianapolis, IN (US); Robert Jason Herr, Voorheesville, NY (US); Muralikrishna Valluri, Rensselaer, NY (US)

(73) Assignee: Emisphere Technologies, Inc., Roseland, NJ (US)

(*) Notice: Subject to any disclaimer, the term of this patent is extended or adjusted under 35 U.S.C. 154(b) by 0 days.

(21) Appl. No.: 13/087,255

(22) Filed: Apr. 14, 2011

(65) Prior Publication Data

US 2011/0190205 A1    Aug. 4, 2011

Related U.S. Application Data

(63) Continuation of application No. 12/263,722, filed on Nov. 3, 2008, now Pat. No. 7,947,841, which is a continuation of application No. 10/566,012, filed as application No. PCT/US2004/024387 on Aug. 18, 2004, now abandoned.

(60) Provisional application No. 60/496,537, filed on Aug. 20, 2003.

(51) Int. Cl.
*C07D 271/06*    (2006.01)
*C07D 401/00*    (2006.01)
*C07D 409/00*    (2006.01)

(52) U.S. Cl.
USPC ............... 548/131; 546/268.4; 549/59

(58) Field of Classification Search
USPC ............... 548/131; 549/59; 546/268.4
See application file for complete search history.

(56) References Cited

U.S. PATENT DOCUMENTS

| | | |
|---|---|---|
| 4,239,754 A | 12/1980 | Sache et al. |
| 4,925,673 A | 5/1990 | Steiner et al. |
| 5,273,989 A | 12/1993 | Schwab et al. |
| 5,541,155 A | 7/1996 | Leone-Bay et al. |
| 5,643,957 A | 7/1997 | Leone-Bay et al. |
| 5,650,386 A | 7/1997 | Leone-Bay et al. |
| 5,693,338 A | 12/1997 | Milstein |
| 5,820,881 A | 10/1998 | Milstein |
| 5,866,536 A | 2/1999 | Leone-Bay et al. |
| 5,965,121 A | 10/1999 | Leone-Bay et al. |
| 5,976,569 A | 11/1999 | Milstein |
| 5,989,539 A | 11/1999 | Leone-Bay et al. |
| 6,001,347 A | 12/1999 | Leone-Bay et al. |
| 6,071,510 A | 6/2000 | Leone-Bay et al. |
| 6,100,298 A | 8/2000 | Leone-Bay et al. |
| 6,211,215 B1 | 4/2001 | Momose et al. |
| 6,242,495 B1 | 6/2001 | Leone-Bay et al. |
| 6,294,580 B1 | 9/2001 | Willson et al. |
| 6,605,629 B1 | 8/2003 | Momose et al. |
| 6,903,085 B1 | 6/2005 | Thom et al. |
| 6,924,284 B2 | 8/2005 | Beaton et al. |
| 6,930,120 B2 | 8/2005 | Brooks et al. |
| 6,982,278 B2 | 1/2006 | Brooks et al. |
| 7,022,725 B2 | 4/2006 | Momose et al. |
| 7,351,728 B2 | 4/2008 | Brooks et al. |
| 2004/0048908 A1 | 3/2004 | Momose et al. |
| 2004/0077557 A1 | 4/2004 | Ali et al. |

FOREIGN PATENT DOCUMENTS

| | | |
|---|---|---|
| GB | 1129393 A | 10/1968 |
| GB | 2373186 A | 9/2002 |
| JP | 1160571 A | 4/1980 |
| JP | 4234857 A | 8/1992 |
| JP | 2002212171 A | 7/2002 |
| JP | 2003144984 A | 5/2003 |
| JP | 2004277397 A | 10/2004 |
| JP | 2004531471 T | 10/2004 |
| WO | WO-9803505 A2 | 1/1998 |
| WO | WO-0040203 A2 | 7/2000 |
| WO | WO-0047188 A1 | 8/2000 |
| WO | WO-0050386 A1 | 8/2000 |
| WO | WO-0059863 A1 | 10/2000 |
| WO | WO-0132130 A2 | 5/2001 |
| WO | WO-0144199 A1 | 6/2001 |
| WO | WO-0151454 A1 | 7/2001 |
| WO | WO-0202509 A1 | 1/2002 |
| WO | WO 0250091 * | 6/2002 |
| WO | WO-02064607 A1 | 8/2002 |
| WO | WO-02096359 A2 | 12/2002 |
| WO | WO-03015785 A1 | 2/2003 |
| WO | WO-03057215 A1 | 7/2003 |
| WO | WO-03072195 A2 | 9/2003 |

OTHER PUBLICATIONS

ACTA Chemica Scandinavica, (1972), 26(2), p. 541-548.
J. Med. Chem., (1970), 13(4), p. 725-729.
Dai, Y, et al. "A Novel Series of Histone Deacetylase Inhibitors Incorporating Hetero Aromatic Ring Systems as Connection Units." Science Direct, Bioorganic and Medicinal Chemistry Letters 13, pp. 3817-3820, 2003.
Patel, H. et al., "Oral Administration of Insulin by Encapsulation within Liposomes." FEBS Letters, vol. 62, No. 1, pp. 60-63, 1976.
Hashimoto, A. et al., "Effects of Oral Administration of Positively Charged Insulin Liposomes on Alloxan Diabetic Rats: Preliminary Study." Endocrinology Japan, vol. 26, No. 3, pp. 337-344, 1979.
International Search Report and Written Opinion of International Application No. PCT/US2004/024387, filed Aug. 18, 2004, mailed on Dec. 12, 2004.
Moriya, et al. Journal of Medicinal Chemistry (1988), 31 (6), 1197-1204.

(Continued)

*Primary Examiner* — Nizal Chandrakumar
(74) *Attorney, Agent, or Firm* — Blank Rome LLP

(57) ABSTRACT

The present application relates to novel compounds, methods and formulations useful for the oral delivery of a glucagon like peptide-1 compound or a melanocortin 4 receptor agonist peptide.

13 Claims, No Drawings

(56) References Cited

OTHER PUBLICATIONS

Janda et al. STN Accession No: 2002-29404; Document No. 136:340636; Abstract of Heterocyclic Communications (2001) 7 (5), 411-416.

Lahkvich et al., STN Document No. 122:105728, Abstract of Medneleev Communications (1994), (6), 227-228.

* cited by examiner

COMPOUNDS, METHODS AND FORMULATIONS FOR THE ORAL DELIVERY OF A GLUCAGON-LIKE PEPTIDE (GLP)-1 COMPOUND OR A MELANOCORTIN-4 RECEPTOR (MC4) AGONIST PEPTIDE

This application is a continuation of U.S. patent application Ser. No. 12/263,722, filed Nov. 3, 2008, which is a continuation of U.S. patent application Ser. No. 10/566,012, filed Jan. 25, 2006, now abandoned, which is a national phase of PCT Application No. PCT/US04/24387, filed Aug. 18, 2004, which claims the benefit of U.S. Provisional Application No. 60/496,537, filed Aug. 20, 2003, all of which are hereby incorporated by reference.

BACKGROUND OF THE INVENTION

Conventional means for delivering active agents are often severely limited by biological, chemical, and physical barriers. Typically, these barriers are imposed by the environment through which delivery occurs, the environment of the target for delivery, or the target itself. Biologically or chemically active agents are particularly vulnerable to such barriers. In the delivery to animals of biologically active or chemically active pharmacological and therapeutic agents, physical and chemical barriers are imposed by the body. Examples of physical barriers are the skin and various organ membranes that must be traversed before reaching a target, and examples of chemical barriers include, but are not limited to, variations in pH, lipid bilayers, and degrading enzymes.

These barriers are of particular significance in the design of oral delivery systems. Oral delivery of many biologically or chemically active agents would be the route of choice for administration to animals if not for biological, chemical, and physical barriers such as varying pH in the gastrointestinal (GI) tract, powerful digestive enzymes, and active agent impermeable gastrointestinal membranes. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents are rapidly rendered ineffective or are destroyed in the gastrointestinal tract by acid hydrolysis, enzymes, or the like.

Earlier methods for orally administering vulnerable pharmacological agents have relied on the co-administration of excipients or enhancers (e.g., resorcinols and non-ionic surfactants such as polyoxyethylene oleyl ether and n-hexadecylpolyethylene ether) to increase artificially the permeability of the intestinal walls, as well as the co-administration of enzyme inhibitors (e.g., pancreatic trypsin inhibitors, diisopropylfluorophosphate) to inhibit enzymatic degradation.

Liposomes have also been described as drug delivery systems for insulin and heparin. See, for example, U.S. Pat. No. 4,239,754; Patel et al (1976), FEBS Letters, Vol 62, pg. 60, and Hashimoto et al. (1970), Endocrinology Japan, Vol, 26, pg. 337.

However, broad spectrum use of such drug delivery systems is precluded because: (1) the systems require toxic amounts of excipients, enhancers or inhibitors; (2) suitable low molecular weight cargos, i.e. active agents, are not available; (3) they exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, microspheres of artificial polymers of mixed amino acids (proteinoids) have been used to deliver pharmaceuticals. For example, U.S. Pat. No. 4,925,673 describes drug-containing proteinoid microsphere carriers as well as methods for their preparation and use. These proteinoid microspheres are useful for the delivery of a number of active agents.

Delivery agent molecules have also been disclosed in U.S. Pat. Nos. 5,541,155; 5,693,338; 5,976,569; 5,643,957; 5,955,503; 6,100,298; 5,650,386; 5,866,536; 5,965,121; 5,989,539; 6,001,347; 6,071,510; 5,820,881; and 6,242,495; see also WO 02/02509; WO 01/51454; WO 01/44199; WO 01/32130; WO 00/59863; WO 00/50386; WO 00/47188; and WO 00/40203.

BRIEF SUMMARY OF THE INVENTION

The present invention relates to a compound of formula I:

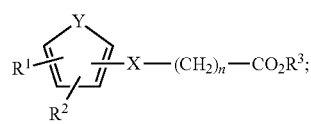

wherein:
$R^1$ and $R^2$ are each independently H, OH, cyano, $C_1$-$C_6$ alkyl, $C_1$-$C_6$ alkoxy, $CF_3$, halo or $NR^4R^{4'}$;
$R^3$ is H, $C_1$-$C_6$ alkyl;
X is a 5 membered aromatic heterocycle that is optionally substituted with $C_1$-$C_4$ alkyl; wherein said heterocycle contains at least two or three heteroatoms selected from N, S and O wherein at least one heteroatom must be N;
Y is S, $CR^5$=N or N=$CR^5$;
n is 2, 3, 4, 5, 6 or 7;
$R^4$ is H, CORE, $SO_2R^7$, or $C_1$-$C_6$ alkyl;
$R^{4'}$ is H or $C_1$-$C_6$ alkyl;
$R^5$ is H or forms a bond with X;
$R^6$ is H or $C_1$-$C_6$ alkyl; and
$R^7$ is H or $C_1$-$C_6$ alkyl; or a pharmaceutical salt thereof.

The present invention further relates to a compound of formula I wherein $R^3$ is H. This compound is hereafter referred to as a compound of formula II.

The present invention also relates to a pharmaceutical composition containing a compound of formula II, or a pharmaceutical salt thereof, and a pharmaceutical carrier.

The present invention also relates to a pharmaceutical composition containing a compound of formula II, or a pharmaceutical salt thereof, and a GLP-1 compound.

The present invention also relates to a pharmaceutical composition containing a compound of formula II, or a pharmaceutical salt thereof, and a MC4 agonist peptide.

DETAILED DESCRIPTION OF THE INVENTION

Reference hereafter to "a compound of formula I" or "compound of formula II" includes the pharmaceutical salts thereof.

For the purposes of the present invention, as disclosed and claimed herein, the following terms are defined below.

The term "halo" refers to fluoro, chloro, bromo and iodo. The term "$C_1$-$C_6$ alkyl" represents a straight, branched or cyclic hydrocarbon moiety having from one to six carbon atoms, e.g., methyl, ethyl, n-propyl, isopropyl, cyclopropyl, n-butyl, isobutyl, sec-butyl, t-butyl, cyclobutyl, pentyl, cyclopentyl, hexyl, cyclohexyl and the like. Moieties such as a cyclobutylmethylene are also included within the scope of a $C_1$-$C_6$ alkyl group. The term "$C_1$-$C_4$ alkyl" refers specifically to methyl, ethyl, n-propyl, isopropyl, cyclopropyl, cyclopropylmethyl, n-butyl, isobutyl, sec-butyl, t-butyl and cyclobutyl. A "$C_1$-$C_6$ alkoxy" group is a $C_1$-$C_6$ alkyl moiety connected through an oxy linkage.

The term "pharmaceutical" when used herein as an adjective means substantially non-deleterious to the recipient patient.

The term "patient" includes humans and non-human animals such as companion animals (dogs, cats, horses and the like). The preferred patient of treatment is a human.

The term "GLP-1 compound" as used herein refers to one or more naturally occurring GLP-1 polypeptides (GLP-1(7-37)OH and GLP-1(7-36)NH$_2$), GLP-1 fragments, GLP-1 analogs, GLP-1 derivatives of naturally occurring GLP-1 polypeptides, GLP-1 fragments, or GLP-1 analogs, and Exendin-3 and Exendin-4 that have the ability to bind to the GLP-1 receptor and initiate a signal transduction pathway resulting in insulinotropic activity as described in PCT Publication Number WO 03/072195 (Application Number PCT/US03/03111); herein incorporated by reference.

The term "MC4 agonist peptide" as used herein refers to the pharmaceutically useful peptides disclosed in PCT Patent Application No. PCT/US04/16625, filed Jun. 17, 2004 (peptides of formula I, II and III as disclosed therein).

The compound of formula II is useful for increasing the oral bioavailability of an active agent, i.e., a GLP-1 compound or an MC4 agonist peptide, when said compound is mixed with the active agent to form a combination composition. Said combination is one embodiment of the present invention. The compositions of the present invention comprise a compound of formula II, that is, a delivery agent (a formula II compound), and a GLP-1 compound or an MC4 agonist peptide.

The present invention is particularly advantageous for delivering a GLP-1 compound or an MC4 agonist peptide (active agent) that would otherwise be destroyed or rendered less effective by conditions encountered before the active agent reaches its target zone (i.e. the area in which the active agent of the delivery composition is to be released) and within the body of the animal to which it is administered. The compositions comprising one or more compounds of formula II (preferably and most typically one) and an active agent have utility in the delivery of said active agent to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery) or over a period of time (such as sustained delivery).

Preferred Compounds (Embodiments) of the Invention

Certain compounds of the invention are particularly interesting and are preferred. The following listing sets out several groups of preferred compounds. It will be understood that each of the listings may be combined with other listings to create additional groups of preferred compounds.

n is 2, 3, 4 or 5;
$R^1$ and $R^2$ are each independently H, OH, OCH$_3$CH$_3$, CF$_3$, Cl, or Br;
$R^1$ and $R^2$ are each independently H, OH, OCH$_3$CH$_3$ or CF$_3$;
$R^1$ and $R^2$ are each independently H, OH, OCH$_3$ or NH$_2$;
$R^1$ is H and $R^2$ is OH;
$R^1$ and $R^2$ are both H;
$R^3$ is H;
$R^4$ is H;
$R^4$ is CORE and $R^6$ is CH$_3$;
$R^4$ is SO$_2$R$^7$ and $R^7$ is CH$_3$;
$R^{4'}$ is H;
$R^7$ is $C_1$-$C_6$ alkyl;
X is

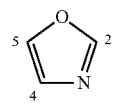

and the aryl (pyridine or thiophene) substituent is attached at carbon atom number 4 and the alkanoic acid chain is attached at carbon atom number 2;

X is

and the aryl substituent is attached at carbon atom number 3 and the alkanoic acid is attached at carbon atom number 5.

PREPARATIONS AND EXAMPLES

All non-aqueous reactions are performed under a dry atmosphere of nitrogen unless otherwise specified. Commercial grade reagents and anhydrous solvents are used as received from vendors and no attempts are made to purify or dry these components further. Removal of solvents under reduced pressure is accomplished with a Buchi rotary evaporator at approximately 28 mm Hg pressure using a Teflon-lined KNF vacuum pump. Thin layer chromatography is performed using 1"×3" Analtech No. 02521, Whatman No. MK6F or EM Science (Merck) No: 5719-2 silica gel plates with fluorescent indicator. Visualization of TLC plates is made by observation with either short wave UV light, 10% phosphornolybdic acid in ethanol or in iodine vapors. Flash column chromatography is carried out using Kieselgel silica gel 60. Proton NMR spectra are obtained on a Broker AC 300 MHz Nuclear Magnetic Resonance Spectrometer and are reported in ppm δ values, using tetramethylsilane as an internal reference. Melting points are obtained using an Electrothermal melting point apparatus and are uncorrected. CI Mass spectroscopic analyses are performed on a Shimadzu QP-5000 GC/Mass Spectrometer (methane) by direct injection. API Mass spectroscopic analyses are performed on a Finnegan LCQ Duo Ion Trap or a PESciex API 150EX mass spectrometer, using electro spray ionization (ESI) or atmospheric pressure chemical ionization (APCI). HPLC analyses are conducted using a Waters Symmetry C18, 5 um, WAT046980, 3.9×150 mm column. The elution system consisted of 90:10 (0.1% TFA in H$_2$O)/(0.1% TFA in CH$_3$CN) gradient elution to 10:90 (0.1% TFA in H$_2$O)/(0.1% TFA in CH$_3$CN) over 20 min, followed by 10:90 (0.1% TFA in H$_2$O)/(0.1% TFA in CH$_3$CN) isocratic elution for 10 min, followed by 90:10 (0.1% TFA in H$_2$O)/

Preparation 1

6-Oxo-6-[(N'-(pyridine-2-carbonyl)hydrazino]hexanoic Acid Methyl Ester

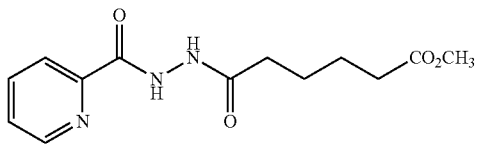 [SMILES: COC(=O)CCCCC(=O)NNC(=O)c1ccccn1]

Stir a solution of 2-picolinylhydrazide (8.05 g, 58.8 mmol) and adipic acid monomethyl chloride (10.5 g, 58.8 mmol) in DMF (117 mL) at room temperature under nitrogen for 12 hours. Remove the solvent under reduced pressure. Triturate the residue with diethyl ether (300 mL), collect the solids by filtration, dissolve in water (200 mL), and wash with ethyl acetate (200 mL). Adjust the pH to 8 with a saturated NaHCO$_3$ solution and extract with ethyl acetate (2×200 mL). Dry the combined organic extracts over sodium sulfate and remove the solvent under reduced pressure to provide 6-oxo-6-[N'-(pyridine-2-carbonyl)hydrazino]hexanoic acid methyl ester (3.85 g, 59%).

Example 1

5-(5-Pyridin-2-yl[1,3,4]oxadiazol-2-yl)pentanoic Acid Methyl Ester

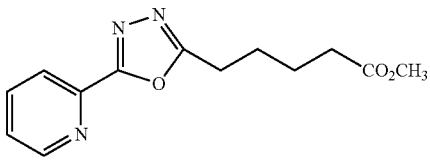 [SMILES: COC(=O)CCCCc1nnc(-c2ccccn2)o1]

Add triethylamine (14.4 mL, 104 mmol) to a mixture of 6-oxo-6-[N'-(pyridine-2-carbonyl)hydrazino]hexanoic octanoic acid methyl ester (9.63 g, 34 mmol), carbon tetrachloride (26.6 g, 172 mmol) and triphenylphosphine (20.3 g, 78 mmol) in acetonitrile (35 mL) at room temperature under nitrogen and stir for 30 minutes. Remove the solids by filtration and then remove the filtrate solvent under reduced pressure. Dilute the residue with water (500 mL) and extract with ethyl acetate (3×500 mL). Wash the combined organic extracts with brine (200 mL), dry over sodium sulfate and remove the solvent under reduced pressure. Triturate the residue with ethyl acetate and collect the solids by filtration to afford 5-(5-pyridin-2-yl[1,3,4]oxadiazol-2-yl)pentanoic acid methyl ester (8.15 g, 91%).

Example 2

5-(5-Pyridin-2-yl[1,3,4]oxadiazol-2-yl)pentanoic Acid

Add 2 N sodium hydroxide (20 mL) to a solution of 5-(5-pyridin-2-yl[1,3,4]oxadiazol-2-yl)pentanoic acid methyl ester (8.16 g, 31 mmol) in THF (60 mL) and methanol (20 mL) at room temperature under nitrogen and heat the mixture at reflux for 12 hours. Remove the solvent under reduced pressure, dilute the residue with water (500 mL), and wash with ethyl acetate (200 mL). Adjust the pH of the aqueous layer to pH 3 with concentrated HCl and extract with ethyl acetate (3×200 mL). Wash the combined organic extracts with brine (200 mL), dry over sodium sulfate, and remove the solvent under reduced pressure to afford 5-(5-pyridin-2-yl[1,3,4]oxadiazol-2-yl)pentanoic acid (2.05 g, 27%). APCI mass spectrum m/z 246 $[C_{12}H_{13}N_3O_3+H]^+$.

Example 3

8-(3-Pyridin-2-yl[1,2,4]oxadiazol-5-yl)octanoic Acid

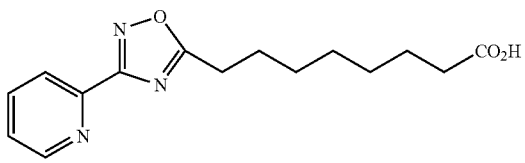 [SMILES: O=C(O)CCCCCCCc1nc(-c2ccccn2)no1]

Add 2 N sodium hydroxide (20 mL) to a solution of ethyl 8-(3-pyridin-2-yl[1,2,4]oxadiazol-5-yl)octanoate in methanol (100 mL) at room temperature under nitrogen and stir the mixture for 3 hours. Remove the solvent under reduced pressure, dilute the residue with water and wash with diethyl ether. Adjust the aqueous layer to pH 1 with 2 N HCl and collect the solids by vacuum filtration to afford the title compound. APCI mass spectrum m/z 288 $[C_{15}H_{19}N_3O_3-H]^-$.

Preparation 2

Methyl 2-Oxo-2-thiophen-3-yl Hexanedioate

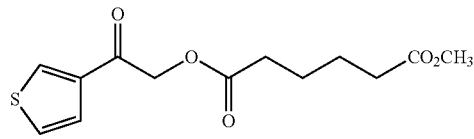 [SMILES: COC(=O)CCCCC(=O)OCC(=O)c1ccsc1]

Add a solution of sodium bicarbonate in water to a solution of suberic acid monomethyl ester in methanol (50 mL) at room temperature and stir the mixture for 30 minutes. Remove the solvent under reduced pressure and add the residue to a solution of 2-bromo-1-thiophen-3-ylethanone in acetone at room temperature under nitrogen. Heat the mixture at reflux for 10 hours and then remove the solvent under reduced pressure. Dilute the residue with diethyl ether, stir for 20 minutes, filter through a short silica gel column, and wash twice with diethyl ether. Remove the solvent under reduced pressure to provide the title compound.

Example 4

Methyl 5-(4-Thiophen-3-yloxazol-2-yl)pentanoate

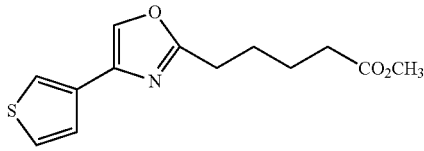 [SMILES: COC(=O)CCCCc1nc(-c2ccsc2)co1]

Heat a mixture of methyl 2-oxo-2-thiophen-3-yl hexanedioate, acetamide and boron trifluoride diethyl etherate at 135-140° C. under nitrogen for 4 hours. Cool the mixture, dilute with saturated NaHCO₃ solution, and extract with ethyl acetate. Wash the organic extract with saturated aqueous sodium chloride (brine) and dry over sodium sulfate. Remove the solvent under reduced pressure and purify the residue by flash column chromatography on silica gel, eluting with hexanes/ethyl acetate to provide the title compound. APCI mass spectrum m/z 266 [C13H15NO3S+H]+.

Example 5

5-(4-Thiophen-3-yl-oxazol-2-yl)pentanoic Acid

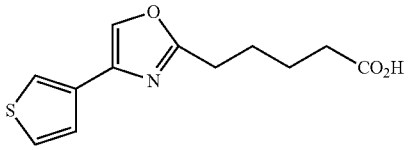 [SMILES: O=C(O)CCCCc1nc(-c2ccsc2)co1]

Add solution of sodium hydroxide in water to a solution of methyl 5-(4-thiophen-3-yloxazol-2-yl)pentanoate in methanol at room temperature and heat the mixture at 40° C. for 2 hours. Adjust the pH of the mixture to 2 with 1 N HCl and extract with ethyl acetate. Wash the organic extract three times with water, dry over sodium sulfate and remove the solvent under reduced pressure. Triturate the residue with hexanes/ethyl acetate and collect the solids by filtration to provide the title compound: APCI mass spectrum m/z 252 [$C_{12}H_{13}NO_3S+H$]+.

Prepare Examples 6-11, compounds of formula II(a) listed in Table 1 below, by the same process as described for the preparation of the compound of Example 6.

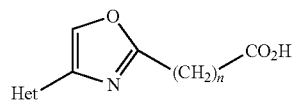

TABLE 1

Compounds of formula II(a)

| Example | Het | n | mass spectrum m/z |
|---|---|---|---|
| 6 | thien-2-yl | 4 | 252 [$C_{12}H_{13}NO_3S + H$]+ |
| 7 | pyrid-2-yl | 4 | 247 [$C_{13}H_{14}N_2O_3 + H$]+ |
| 8 | 3-hydroxy-thien-2-yl | 4 | 268 [$C_{12}H_{13}NO_4S + H$]+ |
| 9 | pyrid-3-yl | 4 | 247 [$C_{13}H_{14}N_2O_3 + H$]+ |
| 10 | pyrid-4-yl | 4 | 247 [$C_{13}H_{14}N_2O_3 + H$]+ |
| 11 | 3-hydroxy-thien-2-yl | 2 | 238 [C10H9NO4S − H]− |

Preparation 3

2-Bromo-1-(3-methoxy-pyridin-2-yl)-ethanone

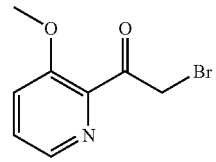

Add sodium hydride (5.91 g, 147.8 mmol) to a rapidly stirred solution of 2-bromo-3-pyridinol in DMF (anhydrous, 200 mL). After 30 minutes, add iodomethane (9.2 mL, 147.8 mmol) and stir under N₂ for 2.5 hours. Quench with water and concentrate. Partition residue between Et₂O and water, separate layers. Extract from aqueous layer with Et₂O (×2), dry combined layers over MgSO₄ and concentrate. Purify residue by flash chromatography on silica gel eluting with 0-25% EtOAc/hexanes to afford 2-bromo-3-methoxy-pyridine (21.0 g, 83%).

Add copper (I) iodide (38 mg, 0.2 mmol) to a mixture of 2-bromo-3-methoxy-pyridine (188 mg, 1.0 mmol), tributyl (1-ethoxyvinyl)tin (0.68 mL, 2.0 mmol), and DMF (anhydrous, 4 mL) in a sealed tube. Flush with N₂, seal, heat at 80° C. for 3 h. Purify the mixture by flash chromatography on silica gel eluting with 0-30% EtOAc/hexanes to afford 2-(1-ethoxy-vinyl)-3-methoxy-pyridine (151 mg, 84%).

Add N-bromo-succinimide (306 mg, 1.7 mmol) to a stirred solution of 2-(1-ethoxy-vinyl)-3-methoxy-pyridine (305 mg, 1.7 mg) in THF (30 mL) and water (2 mL). Stir for 15 mins. at RT under N₂. Adsorb on SiO₂ and purify by flash chromatography on silica gel eluting with 0-40% EtOAc/hexanes to afford the title compound (211 mg, 54%).

Example 12

5-[(4-(3-Methoxy-pyridin-2-yl)-oxazol-2-yl]-pentanoic acid methyl ester

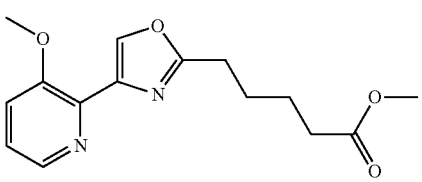 [SMILES: COC(=O)CCCCc1nc(-c2ncccc2OC)co1]

Add boron trifluoride etherate (0.30 mL, 1.00 mmol) to a sealed tube containing 2-bromo-1-(3-methoxy-pyridin-2-yl)- ethanone (231 mg, 1.00 mmol), 5-carbamoyl-pentanoic acid methyl ester (222 mg, 1.39 mmol), and THF (anhydrous, 3 mL). Flush with $N_2$, seal, heat at 80° C. overnight. Partition between saturated aqueous $NaHCO_3$ solution and 20% i-PrOH/$CHCl_3$, separate layers. Extract from aqueous layer with 20% i-PrOH/$CHCl_3$ (×3), dry combined organic layers with $MgSO_4$ and concentrate. Adsorb on $SiO_2$ and purify by flash chromatography on silica gel eluting with 1-3% methanol/$CHCl_3$ to afford the title compound (97 mg, 33%). MS (IS) 291 (M+1)$^+$.

Example 13

5-[4-(3-Hydroxy-pyridin-2-yl)-oxazol-2-yl]-pentanoic acid

Treat 5-[4-(3-methoxy-pyridin-2-yl)-oxazol-2-yl]-pentanoic acid methyl ester with boron tribromide followed by standard hydrolysis to afford the title compound.

Formulation

Because the compound of formula II may contain a basic and/or acidic moiety (i.e., amino and/or carboxylic acid), said compound may be formulated as a pharmaceutical salt, e.g., as the sodium or hydrochloride salt or as a salt described in "Handbook of Pharmaceutical Salts: Properties, Selection and Use", Weinheim, N.Y.: VHCA; Wiley-VCH, 2002. The compound of formula II is preferably formulated in a dosage unit form, i.e., in an individual delivery vehicle, for example, a tablet or capsule, prior to administration to the recipient patient. Therefore, yet another embodiment of the present invention is a pharmaceutical composition comprising a compound of formula II, or a pharmaceutical salt thereof, an active agent, and a pharmaceutical carrier.

The present pharmaceutical compositions are prepared by known procedures using well-known and readily available ingredients. In making the formulations of the present invention, the delivery agent (formula II compound) will be mixed with an active agent and will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient.

Biological Assays

Delivery Agent Formulation Development

For oral dosing of a GLP-1 compound, a pH range of 7.4 to 8.4 for each formulation is typically employed, whereas for a MC4 agonist peptide, a pH range of 6.8-7.2 (most typically 7.0) for the formulation of is typically utilized. A target delivery agent concentration of 150 mg/mL in both cases is also typical. Initial feasibility studies are conducted to determine final carrier formulations.

Briefly, 200 mg of delivery agent is weighed into a Type I glass vial, to which 1 mL of MilliQ water is added. Each mixture is visually inspected for solubility, followed by addition of NaOH to increase solubility or HCl to decrease the pH to the oral dose range. Formulations are then diluted to 150 mg/mL with MilliQ water. Using this approach, the formulations generally fell into three categories: aqueous soluble, nearly completely soluble (e.g., few undissolved particles remaining, very fine aqueous suspensions or hazy suspensions), and aqueous insoluble (e.g., heavy suspensions). Delivery agents that exhibited aqueous insolubility are formulated in 4% w/v (aqueous) hydroxypropylcellulose (Klucel® LF, Hercules, Wilmington, Del.) as needed. In these cases, between 50 and 100 mg of agent is suspended in Klucel® LF in a Type I glass vial, to yield a concentration of 200 mg/mL. For heavy aqueous and Klucel® LF suspensions, the preparations are cooled on ice for 3 minutes, followed by probe sonication on ice for 30 minutes using a Misonix Sonicator® Ultrasonic Processor XL ($^3/_{16}{}^{th}$ inch microtip) to reduce particle size. Following pH adjustment with NaOH or HCl, the formulations are then diluted to 150 mg/mL with MilliQ water or Klucel® LF.

Formulation of Stock Active Agent Solution

The GLP-1 compounds (e.g., Val$^8$-Glu$^{22}$-GLP-1(7-37)OH and Val$^8$-Glu$^{22}$-I$^{33}$-GLP-1(7-37)OH) and MC4 agonist peptides (e.g., Ac-Arg-cyclo[Cys-Glu-His-D-Phe-Arg-Trp-Cys]-$NH_2$; Ac-cyclo[hCys-His-D-Phe-Arg-Trp-Cys]-$NH_2$; Ac-cyclo[hCys-His-D-Phe-Arg-Trp-penicillamine]-$NH_2$; and N-cyclohexanecarbonyl-cyclo[hCys-His-D-Phe-Arg-Trp-penicillamine]-$NH_2$) used herein are described in PCT Publication Number WO 03/072195 and PCT Patent Application No. PCT/US04/16625, filed June 17, respectively.

A stock solution of GLP-1 compound active agent is prepared as follows. Briefly, a known quantity of lyophilized active agent is weighed into a Type I glass vial. MilliQ water is then added to yield an initial concentration of about 7-10 mg/mL. Complete solubility of the peptide is achieved by slowly raising the pH of the medium to 10.5 with 1 N NaOH and 5 N NaOH, followed by incubation at room temperature for 30 minutes. A volume of 1 M Tris buffer, pH 8.0 is added to give a final buffer concentration of 20 mM Tris, and the pH adjusted to pH 7.8 with 1N HCl and 5 N HCl. The solution is then filtered through a low protein binding 0.22 μM syringe filter (Millex GV, Millipore). The concentration of the peptide filtrate is determined by UV spectroscopy ($\lambda$ max=280 nm). The solution is then diluted to a stock concentration of about 5.0 mg/mL using 20 mM Tris buffer, pH 7.8. The active agent solution is stored in 1.0 mL aliquots at −70° C. until used.

A stock solution of MC4R agonist peptide is prepared as follows. Briefly, a known quantity of lyophilized MC4R agonist peptide is weighed into a Type I glass vial. MilliQ water is then added to yield an initial concentration of about 19-21 mg/mL. The pH is raised to 6.0 with 1 N NaOH and 5 N NaOH, followed by incubation at room temperature for 30 minutes. The concentration of the peptide solution is determined by UV spectroscopy (max=280 nm; light scatter correction applied between 250 nm and 410 nm). The solution is then stored as a stock, concentration of about 20.0 mg/mL. The peptide solution is stored, refrigerated 4-8° C. until used.

Rat Oral Delivery Method

Male Sprague-Dawley (femoral artery cannulated, Charles River, Wilmington, Mass.) rats weighing 250-300 g are used in these studies. Animals are housed in single house stainless steel cages and cared for according to Eli Lilly and Company Animal Care and Use Policies & Procedures. Animals are fasted for at least 12 hours (with free access to water) before dose administration. Each experiment (delivery agent+active agent) is conducted in a group of four rats. Final formulations for each delivery agent are freshly prepared approximately 5-10 minutes prior to in vivo dosing.

Specifically, delivery agent formulation (~165 mg/mL stock) and GLP-1 compound active agent solution (~5.0 mg/mL stock) are added together to yield an admixture of delivery agent active agent. The final concentrations in each such formulation are 150 mg/mL and 0.5 mg/mL, respectively. Formulations are dosed by oral gavage (PO) for a final dose of 300 mg/kg delivery agent and 1.0 mg/kg active agent. One mL of blood samples is collected in EDTA tubes from the systemic (femoral artery) cannula from each animal (one sample/time point) at 5, 10, and 20 minutes: Tubes are chilled on ice immediately following collection and centrifuged at approximately 5° C./3,000 rpm/15 minutes. Plasma is removed, transferred into 12×75 mm polypropylene sample tubes with snap caps, and stored immediately at −70° C. until analyzed by a radioimmunoassay.

In the case of an MC4 agonist peptide active agent, delivery agent formulation (~165 mg/mL stock) and peptide solution (~20.0 mg/mL stock) are added together to yield an admixture of delivery agent+active agent. The final concentrations in each such formulation are 150 mg/mL and 5.0 mg/mL, respectively. Formulations are dosed by oral gavage (PO) for a final dose of 300 mg/kg delivery agent and 10.0 mg/kg active agent. 0.40 mL of blood sample is collected in heparin tubes from the systemic (femoral artery) cannula from each animal (one sample/time point) at 5, 15, 30, 60, 90 and 120 minutes. Tubes are chilled on ice immediately following collection and centrifuged at approximately 5° C./3,000 rpm/15 minutes. Plasma is removed, transferred into 96 Well plates and stored immediately at −70 C until analyzed by a LC/MS/MS.

Radioimmunoassay and Pharmacokinetic Analysis

Concentrations of immunoreactive active agent in rat plasma are assayed by a radioimmunoassay assay that nonspecifically detects native peptide and metabolic products. These concentrations are subsequently used to determine the reported pharmacokinetic parameters. Plasma samples are mixed with radiolabeled active agent and rabbit polyclonal antiserum and then incubated overnight at ~4° C. Bound and free forms of immunoreactive active agent are separated by precipitating the bound fraction by polyethylene glycol-assisted, secondary antibody precipitation. After collecting the bound fraction by centrifugation, the radioactivity is measured by a gamma counter. Data is analyzed by a weighted 4/5 parameter logistic algorithm. For GLP-1 compounds, the standard curve ranges from 9.8 pg/mL to 10000 pg/mL and the upper and lower quantification limits are 150 pg/mL and 4000 pg/mL, respectively. For MC4 agonist peptides, the standard curve ranges from 5.0 ng/mL to 5000 ng/mL and the upper and lower quantification limits are 10 ng/mL and 5000 ng/mL, respectively. Pharmacokinetic analysis is performed using WinNonlin™ Version 3.0 (Pharsight Corporation, Mountain View, Calif.). Plasma concentration time data are reported as mean±standard deviation (SD). Delivery agent efficiency is defined as area under the plasma concentration-time curve measured from 0 to 20 min (AUC) of active agent in the presence of each delivery agent. Representative compounds of formula II (delivery agent) are tested with an active agent in the Rat Oral Delivery assay and the AUC of active agent in the presence of delivery agent is greater than the AUC of the active agent in the absence of the delivery agent.

We claim:

1. A compound of formula I:

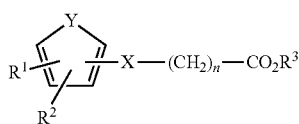

wherein:
R$^1$ and R$^2$ are each independently H, OH, cyano, C$_1$-C$_6$ alkyl, C$_1$-C$_6$ alkoxy, CF$_3$, halo or NR$^4$R$^{4'}$;
R$^3$ is H or C$_1$-C$_6$ alkyl;
X is

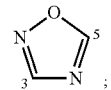

wherein the Y containing cyclic group is attached at position number 3 of the oxadiazole ring X, and the (CH$_2$)$_n$—CO$_2$R$^3$ moiety is attached at position number 5 of the oxadiazole ring X;
Y is S, CR$^5$=N or N=CR$^5$;
n is 5, 6 or 7;
R$^4$ is H, COR$^6$, SO$_2$R$^7$, or C$_1$-C$_6$ alkyl;
R$^{4'}$ is H or C$_1$-C$_6$ alkyl;
R$^5$ is H or forms a bond with X;
R$^6$ is H or C$_1$-C$_6$ alkyl; and
R$^7$ is H or C$_1$-C$_6$ alkyl;
or a pharmaceutically acceptable salt thereof
wherein said compound of formula I is not:

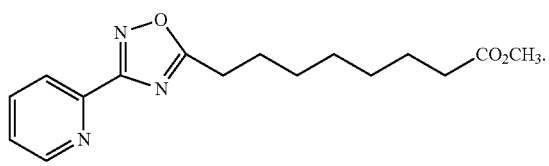 [SMILES: COC(=O)CCCCCCCc1nc(-c2ccccn2)no1]

2. The compound of claim 1 wherein R$^1$ and R$^2$ are each independently H, OH, C$_1$-C$_6$ alkyl, C$_1$-C$_6$ alkoxy, CF$_3$, halo or NR$^4$R$^{4'}$ and wherein X is not substituted with C$_1$-C$_4$ alkyl.

3. The compound of claim 1 wherein R$^3$ is H.

4. A compound which is

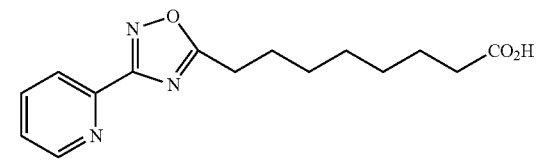 [SMILES: O=C(O)CCCCCCCc1nc(-c2ccccn2)no1]

or a pharmaceutical salt thereof.

5. A pharmaceutical composition comprising:
a) a compound of claim 1; and
b) a GLP-1 compound.

6. The composition of claim 5, wherein the GLP-1 compound is Val$^8$-Glu$^{22}$-GLP-1(7-37)OH.

7. A pharmaceutical composition comprising:
a) a compound of claim 1; and
b) an MC4 agonist peptide.

8. The composition of claim 7, wherein the MC4 agonist peptide is selected from the group consisting of:
Ac-Arg-cyclo[Cys-Glu-His-D-Phe-Arg-Trp-Cys]-NH$_2$;
Ac-cyclo[hCys-His-D-Phe-Arg-Trp-Cys]-NH$_2$;
Ac-cyclo[hCys-His-D-Phe-Arg-Trp-penicillamine]-NH$_2$; and
N-cyclohexanecarbonyl-cyclo[hCys-His-D-Phe-Arg-Trp-penicillamine]-NH$_2$.

9. A pharmaceutical composition comprising:
a) a compound of formula I:

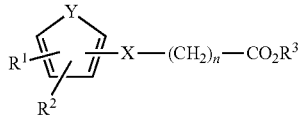

wherein:
- $R^1$ and $R^2$ are each independently H, OH, cyano, $C_1$-$C_6$ alkyl, $C_1$-$C_6$ alkoxy, $CF_3$, halo or $NR^4R^4$;
- $R^3$ is H or $C_1$-$C_6$ alkyl;
- X is

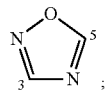

wherein the Y containing cyclic group is attached at position number 3 of the oxadiazole ring X, and the $(CH_2)_n$—$CO_2R^3$ moiety is attached at position number 5 of the oxadiazole ring X;
- Y is S, $CR^5$=N or N=$CR^5$;
- n is 2, 3, 4, 5, 6 or 7;
- $R^4$ is H, $COR^6$, $SO_2R^7$, or $C_1$-$C_6$ alkyl;
- $R^4$ is H or $C_1$-$C_6$ alkyl;
- $R^5$ is H or forms a bond with X;
- $R^6$ is H or $C_1$-$C_6$ alkyl; and
- $R^7$ is H or $C_1$-$C_6$ alkyl;

or a pharmaceutically acceptable salt thereof, wherein said compound of formula I is not:

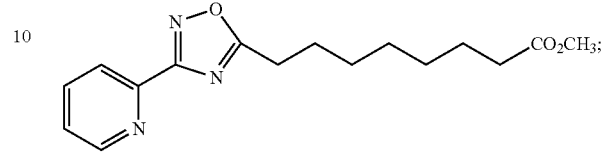

and
b) a pharmaceutically acceptable carrier.

10. The composition of claim 9, further comprising a GLP-1 compound.

11. The composition of claim 9, further comprising an MC4 agonist peptide.

12. The composition of claim 5, wherein the GLP-1 compound is a GLP-1 fragment, GLP-1 analog or GLP-1 derivative.

13. The composition of claim 10, wherein the GLP-1 compound is a GLP-1 fragment, GLP-1 analog or GLP-1 derivative.

* * * * *